US00PP37363P2

(12) United States Plant Patent
Boxriker

(10) Patent No.: US PP37,363 P2
(45) Date of Patent: Apr. 7, 2026

(54) DAHLIA PLANT NAMED 'KLEDH24724'

(50) Latin Name: *Dahlia sp.*
Varietal Denomination: KLEDH24724

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/317,094

(22) Filed: Sep. 2, 2025

(51) Int. Cl.
*A01H 5/02* (2018.01)
*A01H 6/14* (2018.01)

(52) U.S. Cl.
USPC ..... Plt./321

CPC ..... *A01H 6/144* (2018.05); *A01H 5/02* (2013.01)

(58) Field of Classification Search
USPC ..... Plt./321
See application file for complete search history.

(56) References Cited

U.S. PATENT DOCUMENTS

PP32,728 P3 * 1/2021 Klemm ..... A01H 6/144 Plt./321

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new *Dahlia* plant designated 'KLEDH24724' particularly distinguished by light pink flowers with darker shades of pink at the distal quarter of ray florets; and a semi upright plant habit, is disclosed.

1 Drawing Sheet

Genus and species: *Dahlia sp.*
Variety denomination: 'KLEDH24724'.

BACKGROUND

The present invention comprises a new and distinct variety of *Dahlia*, botanically known as *Dahlia* sp., and hereinafter referred to by the variety name 'KLEDH24724'. 'KLEDH24724' originated from an open pollination in a field with the female 'KLEDH18127' (U.S. Plant Pat. No. 32,750) and an unknown male *Dahlia* plant in the summer of 2020 in Latina, Italy. In March 2021 a seedling was selected and named 'KLEDH24724'. 'KLEDH24724' was first vegetatively propagated by vegetative cuttings in May 2021 in Stuttgart, Germany. 'KLEDH24724' was found to reproduce true to type in successive generations of asexual propagation.

SUMMARY

The following are the most outstanding and distinguishing characteristics of 'KLEDH24724' when grown under normal horticultural practices in Latina, Italy.

1. Light pink flowers with darker shades of pink at distal quarter of ray florets; and
2. Semi-upright plant habit.

DESCRIPTION OF THE PHOTOGRAPH

This new *Dahlia* plant is illustrated by the accompanying photograph of the plant approximately fourteen weeks old and grown in a greenhouse in Stuttgart, Germany. The photograph shows the whole plant, unless otherwise noted, including the inflorescences and foliage and buds and was taken in May 2024 in Stuttgart, Germany. The colors shown are as true as can be reasonably obtained by conventional photographic procedures.

DESCRIPTION OF 'KLEDH24724'

The following detailed descriptions set forth the distinctive characteristics of 'KLEDH24724'. The data which define these characteristics were collected from asexual reproductions carried out in Latina, Italy. Data was collected on 16-week-old plants, with one pinch and grown in a greenhouse. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* sp.
- *Designation*.—'KLEDH24724'.

Parentage:
- *Female parent*.—'KLEDH18127' (U.S. Plant Pat. No. 32,750).
- *Male parent*.—Unknown male parent.

Propagation:
- *Type*.—Vegetative terminal cuttings.
- *Time to produce a rooted young plant*.—3 to 4 weeks.
- *Time to produce a flowering plant*.—About 10 weeks.
- *Root description*.—RHS N155C in color, fine.
- *Rooting habit*.—Freely branching and moderately dense.

Plant description:
- *Plant and growth habit*.—Semi-upright.
- *Plant height*.—To the top of foliar plane: About 24 cm. Including inflorescence: About 32 cm.
- *Plant diameter*.—About 38 cm.

Lateral branches:
*Length*.—Up to the last pair of leaves: About 21.0 cm. Including inflorescence: About 30.0 cm.
*Diameter*.—About 0.6 cm.
*Internode length*.—From 4 to 8 cm.
*Strength*.—Strong.
*Texture*.—Smooth.
*Color*.—Close to RHS N77A.

Foliage description:
*Arrangement*.—Opposite.
*Length*.—Up to 16.0 cm.
*Width*.—Up to 12.5 cm.
*Shape*.—Pinnate or approximatively ovate.
*Apex*.—Acute.
*Base*.—Obtuse.
*Margin*.—Serrate.
*Venation pattern*.—Pinnate.
*Venation color*.—RHS N77A.
*Texture*.—Upper and lower surface: Little hairy on the edges, slightly rugose and glossy.
*Color*.—Immature: Upper surface: Close to RHS 147A. Lower surface: Close to RHS 191A. Mature: Upper surface: RHS N137B. Lower surface: RHS 191A.

Petioles:
*Length*.—About 2.7 cm.
*Diameter*.—About 0.4 cm.
*Texture*.—Upper surface: Smooth. Lower surface: Smooth.
*Color*.—Upper surface: Close to RHS 183A. Lower surface: Close to RHS 191A.

Inflorescence description:
*Appearance and arrangement*.—Composite head inflorescence, double, held above the foliage.
*Fragrance*.—Not detected.
*Time to flower*.—About 10 weeks after potting.
*Post-production longevity*.—Plants flower continuously from spring through autumn.

Inflorescence bud:
*Height*.—About 1.0 cm.
*Diameter*.—About 1.3 cm.
*Shape*.—Globular.
*Color*.—RHS 187A.

Inflorescence size:
*Diameter*.—7.5 cm.
*Depth* (*height*).—About 2.0 cm.
*Disc diameter*.—Not visible.
*Receptacle height*.—About 0.8 cm.
*Receptacle diameter*.—About 1.5 cm.
*Receptacle color*.—Close to RHS 143A.

Ray florets:
*Quantity per inflorescence*.—About 92 in about 4 whorls.
*Length*.—3.4 cm.
*Width*.—1.5 cm.
*Shape*.—Oval.
*Apex*.—Slightly dentate.
*Base*.—Fused in a tube.
*Margin*.—Entire.
*Aspect*.—Keeled.
*Texture*.—Upper surface.—Smooth. Lower surface.—Smooth.
*Color*.—Immature: Upper surface: RHS 75D at the base with RHS 72A to RHS 72B toward the distal quarter. Lower surface: RHS close to 159D at the base with RHS 77A toward the distal quarter. Mature: Upper surface: RHS 75D at the base with RHS 72A to RHS 72B toward the distal quarter. Lower surface: RHS close to RHS 75D at the base with RHS N78B toward the distal quarter.

Disc florets:
*Quantity per inflorescence*.—About 40.
*Length*.—About 0.8 cm.
*Diameter*.—About 0.15 cm.
*Shape*.—Tubular.
*Texture*.—Inner surface: Smooth. Outer surface: Smooth.
*Color*.—Immature: Inner surface: RHS N144B at base with a gradient of RHS 172C at the tip. Outer surface: RHS N144A at base with a gradient of RHS 172A at the tip. Mature: Inner surface: RHS N144A at base with a gradient of RHS 183A at the tip. Outer surface: Close to RHS183A.

Phyllaries:
*Quantity per inflorescence*.—7 at the external whorl, 16 in the internal whorls.
*Length*.—About 1.5 cm the external ones, about 2.0 cm the inner ones.
*Width*.—About 0.4 cm the external ones, about 0.7 cm the inner ones.
*Shape*.—Lanceolate to spatulate.
*Apex*.—Acute.
*Base*.—Attenuate the external ones, fused the internal whorls.
*Margin*.—Entire.
*Texture*.—Upper surface: Smooth and slightly glossy. Lower surface: Smooth and slightly glossy.
*Color*.—Upper surface: external whorl: RHS N137A. internal whorl: RHS 147A at the base to N79B at the tips. Lower surface: external whorl: RHS N137B. internal whorl: RHS 147A at the base to N79B at the tips.

Peduncles:
*Length, terminal peduncle*.—Around 10.0 cm.
*Length, axillary peduncle*.—Around 5.0 cm.
*Diameter*.—0.3 cm.
*Strength*.—Strong.
*Texture*.—Smooth.
*Color*.—RHS N77A.

Reproductive organs:
*Androecium*.—Only on disc florets. Quantity per floret: 5 stamens with fused anthers. Filament length: 0.4 cm. Filament color: RHS 145D. Anther shape: Oblong. Anther length: 0.4 cm. Anther color: RHS 14A. Pollen amount: moderate. Pollen color: RHS 14A.
*Gynoecium*.—Quantity per floret: 1. Pistil length: 1.3 cm. Style length: 0.7 cm. Style color: RHS 1B. Stigma shape: Bipartite. Stigma color: RHS 17A. Ovary color: RHS 145B.

Fruit and seed set: Not observed.

Disease and pest/insect resistance: No disease resistance observed.

COMPARISON OF 'KLEDH24724' WITH PARENTAL LINE AND KNOWN VARIETY

'KLEDH24724' is distinguished from the parent as described in Table 1.

TABLE 1

| Comparison with Parental Line | | |
|---|---|---|
| Trait | Variety 'KLEDH24724' | Female parent |
| Flower color | Light pink with darker shades of pink toward the distal quarter | Pink magenta with creamy center |

'KLEDH24724' can be compared to the commercial *Dahlia* variety 'KLEDH18119' (U.S. Plant Pat. No. 32,728). Differences between the varieties are described in Table 2.

TABLE 2

| Comparison with Similar Variety | | |
|---|---|---|
| Trait | Variety 'KLEDH24724' | Commercial line 'KLEDH18119' |
| Flower color | Light pink with darker shades of pink toward the distal quarter | Dark red |

I claim:

1. A new and distinct variety of *Dahlia* plant designated 'KLEDH24724', as illustrated and described herein.

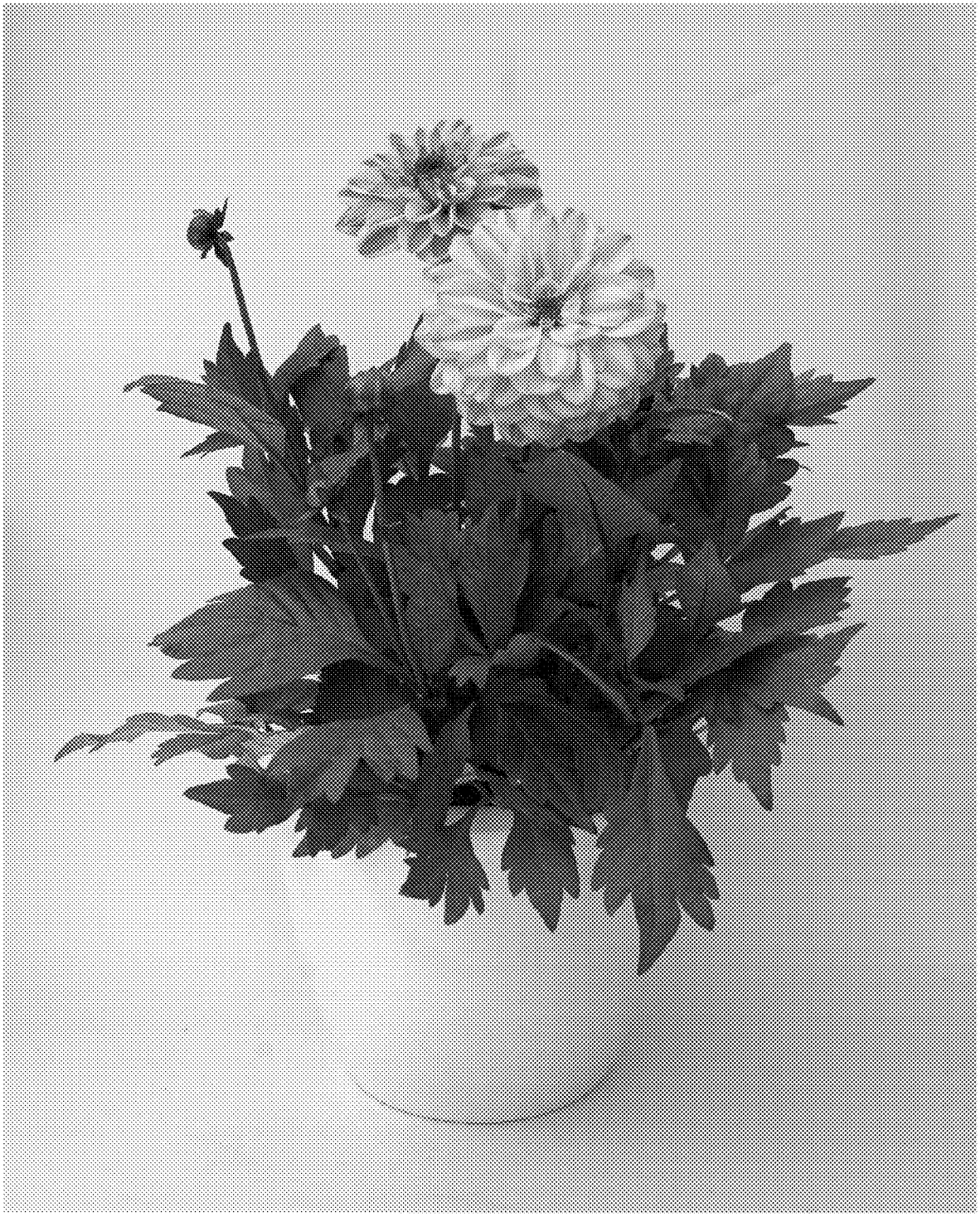

* * * * *